United States Patent
Herold et al.

(12)

(10) Patent No.: US 7,606,667 B2
(45) Date of Patent: Oct. 20, 2009

(54) MASS SPECTROMETRY ANALYSIS METHOD AND SYSTEM

(75) Inventors: Michael Manfred Herold, Berlin (DE); Martin Kluttig, Berlin (DE); Nicole Christiansen, Berlin (DE); Joachim Kopka, Berlin (DE); Jörn Quedenau, Groβ Glienicke (DE)

(73) Assignee: Metanomics GmbH, Berlin (DE)

( * ) Notice: Subject to any disclaimer, the term of this patent is extended or adjusted under 35 U.S.C. 154(b) by 176 days.

(21) Appl. No.: 11/815,220

(22) PCT Filed: Feb. 1, 2006

(86) PCT No.: PCT/EP2006/000883

§ 371 (c)(1),
(2), (4) Date: Aug. 1, 2007

(87) PCT Pub. No.: WO2006/082042

PCT Pub. Date: Aug. 10, 2006

(65) Prior Publication Data

US 2008/0128607 A1 Jun. 5, 2008

(30) Foreign Application Priority Data

Feb. 1, 2005 (EP) .................... 05100825

(51) Int. Cl.
*G01F 19/00* (2006.01)
(52) U.S. Cl. ............ 702/22; 250/339.07; 324/717
(58) Field of Classification Search ............. 702/22, 702/2, 19, 23, 24, 27, 28, 30, 32, 182–185; 250/339.07, 339.05, 339.06, 339.13, 341.8; 324/717, 310
See application file for complete search history.

(56) References Cited

U.S. PATENT DOCUMENTS

| 5,175,430 A | 12/1992 | Enke et al. |
| 5,453,613 A | 9/1995 | Gray et al. |
| 5,481,476 A * | 1/1996 | Windig ..................... 702/31 |
| 6,147,344 A | 11/2000 | Annis et al. |
| 2005/0165560 A1* | 7/2005 | Kushnir et al. ............... 702/30 |

(Continued)

OTHER PUBLICATIONS

Stein, "An Integrated Method for Spectrum Extraction and Compound Identification from Gas Chromatography/Mass Spectrometry Data", *J Am Soc Mass Spectrom*, vol. 10, pp. 770-781 (1999).

(Continued)

*Primary Examiner*—Edward Raymond
(74) *Attorney, Agent, or Firm*—Connolly Bove Lodge & Hutz LLP

(57) ABSTRACT

The invention relates to a method and device for analyzing a sample containing a number of substances. The method comprises the following steps: recording one or more mass spectra (mass spectra data D) of the sample (P); deconvoluting the mass spectra in a first evaluating device (A), which assigns the chromatographic peaks (a) and their associated deconvoluted mass spectra of one substance at a time based on the correspondence with a reference spectrum of the substance, and/or determining the intensity of the obtained peaks of the ions of the mass spectra in an evaluating device (B), which assigns the chromatographic peaks (b) of the ions and their associated mass spectra based on the correspondence of selective ions and their retention time ranges of the peaks (b) with the reference values of the substance predetermined for a substance, and verifying the assignments in a validating device (V).

38 Claims, 9 Drawing Sheets

OTHER PUBLICATIONS

Stan, "Pesticide residue analysis in foodstuffs applying capillary gas chromatography with mass spectrometric detection State-of-the-art use of modified DFG-multimethod S19 and automated data evaluation", *Journal of Chromatography A*, vol. 892, pp. 347-377 (2000).

"G1701CA MSD Productivity ChemStation", brochure brief, 22 pages (1999), Agilent Technologies.

* cited by examiner

MASS SPECTROMETRY ANALYSIS METHOD AND SYSTEM

PRIORITY

Priority is claimed as a national stage application, under 35 U.S.C. § 371, to PCT/EP2006/000886, filed Feb. 1, 2006, which claims priority to European application 051008258, filed Feb. 1, 2005.

The invention relates to a method for analyzing a sample containing a plurality of substances by means of mass spectroscopy on the sample which has been at least partially separated in an upstream chromatograph, to a corresponding mass spectrometry analysis system, and its use for analyzing a sample containing a plurality of substances, in particular plant extracts.

Mass spectroscopy or mass spectrometry (MS) is a widely used method for identifying substances and/or molecules in both organic chemistry and inorganic chemistry. In mass spectrometry, the ions are separated and recorded on the basis of their mass/charge (m/z) ratio. The separated ions can be recorded either on a photographic plate, or electrically as an ion current. The first case is referred to as mass spectroscopy, and the second case (which is more important for analytical chemistry) as mass spectrometry. The equipment used is referred to in a corresponding manner as a mass spectrograph or a mass spectrometer. In principle, a mass spectrometer comprises three parts: a device for producing ions ("ion source"), a separating apparatus ("analyzer") and, finally, the receiver (Faraday cage, secondary-electron multiplier) for recording the ions. In addition to the electronics required, the accessories include a data processing installation as well as pumps for the vacuum that is required. For clarity reasons, both mass spectrometry and mass spectroscopy are referred to in the following text by the generic expression "mass spectrometry". Mass spectrometry is normally carried out in conjunction with further analysis methods, such as gas chromatography (UC) and liquid chromatography (LC), in order to simplify the analysis of mass spectra by previous separation of the sample. This results in powerful analysis equipment which, in simple terms, simplifies the analysis by delaying the arrival of the individual components in the mass spectrometer. The numbers of molecules or molecule species and ions which are present at the same time in the mass spectrometer and result, for example, from ionization, rearrangement, fragmentation reactions etc. are thus reduced, thus allowing or simplifying the separation of the mass spectra and ion intensity maxima in the time profile (peaks), and their assignment with specific analytes (substances).

The results are normally based on the chromatographic intensity maxima of the detector signal for individual ions or for a plurality of ions (peaks) being integrated by using a predetermined method. The retention time (time from the injection of the sample to the corresponding signal maximum) and additional information such as the characteristic mass spectrum of the substance, which is recorded by the detector during the retention time, are used as criteria for identifying the correct signals in the chromatogram or mass spectra, and for assignment to the correct chemical compounds which are reflected therein.

However, mass-spectrometric analysis of the chromatographic results can fail if two or more components are eluted so close to one another that their retention times scarcely differ from one another and they therefore occur virtually or at the same time in the mass spectrometer. Furthermore, analysis of the results becomes difficult (if not impossible) as soon as the number of substances in the sample rises and, at the same time, the mass spectra of analytes which have not been completely separated chromatographically differ only to a minor extent, or not at all. A situation such as this normally arises during the analysis of sewerage, special waste, organic and biological tissue such as plant extract, where the sample often contains more than 1,000 substances.

In addition, the recorded spectra are frequently "contaminated". By way of example, the contamination originates from the capillary column used in the chromatograph (bleeding of the column material), contamination in the ion source and incorrect handling, that is to say decomposition of the sample.

Programs and methods for searching libraries with reference spectra and comparing them with the data obtained are only of limited assistance in the situations described above.

One method that is used is the extraction of "pure" spectra of the components contained in the mixture. One algorithm which is normally used for this purpose comprises extraction of the spectrum in which the ion signals assigned to that spectrum reach a maximum at the same time, that is to say a spectrum is generated which includes only those mass/intensity pairs whose mass/charge ratios have maxima at or directly adjacent to the selected measurement in the chromatogram. This algorithm is called, after its discoverers, the Biller-Biemann algorithm (J. Biller, K. Biemann, Anal Letters 1974, 7, 515). Although this algorithm is simple to implement, its results provide little assistance because their resolution is inadequate.

A more powerful method is based on analyzing the shape of the peaks, with the assumption being made that all the peaks which are assigned to the same components have the same signal form (R. G. Dromey et al. Anal. Chem. 1976, 48, 1365).

One alternative method is to add peak-form analysis to the Biller-Biemann algorithm and nevertheless to retain its simplicity, in order to allow commercial use (B. N. Colby, J. Am. Soc. Mass Spectrom. 1992, 3, 3558-3562).

These efforts relating to deconvolution of spectra have resulted in methods and commercially available products, such as AMDIS (Automated Mass Spectral Deconvolution & Identification System, U.S. Department of Commerce, National Institute of Standards and Technology (NIST)). This method for automatically finding and distinguishing between as many different components included in the measurement as possible (substances) is described in S. E. Stein, J. Am. Soc. Mass. Spektrom. 1999, 10, 770-781 (and http://chemdata.nist.gov/mass-spc/amdis/method.pdf).

U.S. Pat. No. 6,147,344 discloses a method for automatically analyzing mass-spectrometric data for mixtures of chemical compounds comprising a series of checks in order to eliminate or reduce false peak assignments resulting from background noise, system resolution, system contamination, multiply charged ions and isotope exchange. For this purpose, a mass spectrum is first of all recorded for a control substance, by means of which mass spectra of subsequent samples have statistical background noise and contamination signals removed from them by subtraction. In addition, peaks with a false width or retention time are excluded from further processing and analysis by means of reference spectra comparison, taking account of isotope distributions.

U.S. Pat. No. 5,175,430 teaches a method and an apparatus for carrying out time compression chromatography with array detection in mass spectrometry, in which a mathematical method is used to recover the information which has been lost by compression so that high sensitivity is achieved despite the analysis time being speeded up and the substance identification being improved.

U.S. Pat. No. 5,453,613 discloses a mass spectrometry analysis system for automatic identification, deconvolution and identification of mass spectra. Mass spectra data recorded using conventional methods is first of all reorganized from the chronological sequence on the basis of the ion mass, and is then once again chronologically reorganized within each ion mass grouping. Local peaks or maxima are identified, sorted and split by means of integration for each measured ion mass, so as to produce a set of deconvoluted spectra in which each element in the set represents an identifiable substance. The substances are then identified by means of reference spectra comparison, using conventional statistical comparison methods.

Admittedly, in some cases, these methods allow deconvolution of spectra and subsequent identification of substances contained in the sample on the basis of reference spectra libraries, but they allow this only for known substances with correspondingly known mass spectra for which searches are deliberately carried out. Furthermore, the methods are subject to false assignments so that substances may be falsely identified, particularly in the case of samples with a large number of components.

None of the known methods are able to identify all of the components in a sample on the basis of the data obtained by chromatography and mass spectrometry, to completely deconvolute spectra without errors, and at the same time to also be carried out automatically.

One object of the present invention is therefore to provide a method which is able to use chromatographic and mass-spectrometric data for a sample to reliably identify as far as possible all of the components contained in it (or at least a larger part of them). In addition, the method should be carried out as automatically as possible and should allow reliable handling of peaks of unknown substances, that is to say it should also be possible to record signals for unknown substances and to ensure consistent assignment over a large number of samples.

The invention therefore proposes a method for analyzing a sample containing a plurality of substances, and having the features of claim 1.

Furthermore, the invention proposes a mass spectrometry analysis system having the features of claim 28, a laboratory information management system (LIMS) having the features of claim 31, and use of the method and of the system for analyzing a sample containing a plurality of substances, in particular plant extracts, which often contain many hundred up to several thousand substances, as claimed in claim 32.

The use of the evaluation devices for subsequently checking the assignment of the chromatographic peaks and mass spectra makes it possible to reliably identify all of the known components (or at least a large proportion of them) contained in a sample. In addition, the method can be carried out automatically and allows reliable handling of peaks of unknown substances. Signals from unknown substances are recorded specifically, ensuring consistent assignment over a large number of samples.

The method according to the invention makes it possible for peaks which have not been deliberately searched for (that is to say peaks without a reference spectrum and the position in the chromatogram (retention time, retention index), in particular peaks of unknown substances) to be marked as such and to be passed on for special treatment, thus considerably simplifying and speeding up the finding of new substances, particularly when large amounts of data are involved.

A fundamental distinction is drawn between so-called "chromatographic peaks" and "mass peaks". A chromatographic peak represents a maximum on a distribution/curve over time in the case of chromatographic separation and, ideally, has a Gaussian form. In this case, it is irrelevant whether the peak originates from the profile of the signal over time of a single ion that has been predetermined as being selective, or from a plurality of added ion signals, or from the addition of all the ion signals. (The latter is the so-called TIC peak (TIC: Total Ion Current)).

Mass peaks can be distinguished from these chromatographic peaks as mass signals in a mass spectrum which relate to maxima of the signal intensity over the mass axis within a mass spectrum. The mass spectra are recorded in precisely the same way as chromatograms as an intensity distribution over time, with the ion mass selected for detection being varied over time. However, this time is short in comparison to the duration of chromatography. A complete mass spectrum in general represents only a single time data point in a conventional chromatogram. The maxima within a mass spectrum such as this last, for example, for about 0.3 s and are already normally integrated in the measurement device, for data reduction. Because of the poor mass resolution in the quadrupole detectors that are often used, the mass spectra obtained are stored in the so-called centroid mode, that is to say only one line is presented per intensity maximum in the mass spectrum, including intensity and mass as information, that is to say no longer including any distribution over time. However, the information relating to the time profile (retention time) is not lost, but is stored for the respective mass peak. For the sake of simplicity, the following text uses the expression "mass peak" whenever this relates to a peak in a mass spectrum. In all other cases, the expression "speak" is used to mean a chromatographic peak over the time axis.

By way of example when using mass spectrometers with low mass resolution, that is to say with unit mass resolution, there is normally only one mass peak per Dalton. For the sake of simplicity, only the (integer) unit masses are then still shown in the mass spectra. If a change is once again made back to the chromatogram and a selected selective ion mass (for example 217) is shown chromatographically over time, then this mass can be used selectively for chromatographic integration. However, it is stored, that all of the ions whose centroid (that is to say mass-spectrometric maximum) falls in a range for example from 217−0.3 to 217+0.7 are also included in the chromatographic integration over time.

All methods which are suitable for combination with mass spectrometry can be used as chromatographic methods, for example gas chromatography (GC), liquid chromatography (LC) or high performance (high pressure) liquid chromatography (HPLC).

Mass spectra can be recorded using all known methods and equipment. Quadrupole mass spectrometers, flight-time mass spectrometers, Fourier transform mass spectrometers and sector field devices should be mentioned by way of example. For further embodiments, reference should be made to the Römpp Lexikon Chemie [Chemical Dictionary]—CD Version 2.0, Stuttgart/New York: Georg Thieme Verlag 1999.

In the present application, the expression deconvolution means the extraction of individual ions (mass/charge ratios) from a series of mass spectra, making use of the fact that all of the intensities of the mass/charge ratios of a spectrum of one component change at the same time and uniformly during elution of this component or substance. In other words, the ratios of the intensities of the signals (peaks) to one another remain the same. Two types of deconvolution are possible: on the one hand deconvolution in which the mass spectrometric data is analyzed in order to determine retention times, amounts and identities of the eluting substances without prior knowledge of the sample composition (referred to as forward search), and on the other hand deconvolution in which the amount and retention times of specific target substances are determined by analyzing the shapes of the characteristic mass spectra (referred to as backward search) (see U.S. Pat. No. 5,175,430 column 6, line 16 to column 7, line 28).

The expression intensity measurement means the extraction and integration (determination of the area of a signal) or determination of the signal level of a peak. Methods for this purpose are known to those skilled in the art. For example, the integration can be carried out by means of Fast Fourier transformation.

The data obtained from the mass spectra is normally associated by means of a comparison with reference spectra of (known) substances contained in the sample. Appropriate libraries and commercial programs are available for this purpose, and in some cases are also integrated in the evaluation devices.

By way of example, AMDIS can be used as the first evaluation device and Chemstation can be used as the second evaluation device as evaluation devices which can in each case be used on their own or in conjunction with the validation device.

These two evaluation devices differ from one another in that the second evaluation device (by way of example Chemstation) uses time windows for peak finding, with the peaks that are found being integrated at a predefined ion mass, while in contrast the first evaluation device (for example Amdis) first of all breaks a data record down into individual components and then compares them with predetermined spectra in a library in order to identify the target substances, using the retention index (RI) instead of the retention time (RT). Chemstation (GC/MS-Chemstation, Agilent Technology, Prod. No. G1701 CA), which has been mentioned by way of example, represents typical integration software for three-dimensional measurement data (time, mass, intensity), with the intensity of an ion being determined by integration over time or by means of its maximum height above the base line (with integration parameters such as time windows, threshold values, qualifying masses, etc. being predetermined). In the case of the AMDIS system, which has been mentioned as an example of the first evaluation device, the deconvolution settings and, optionally, reference spectra, RI calibration and RI values for substance identification must be preset (see the Manual at http://chemdata.nist.gov/mass-spc/amdis/AMDIS.pdf).

These two commercially available evaluation devices (or programs) check only the peaks of target substances, that is to say only those target peaks which have already been entered as parameters are specifically searched for. This relates to details relating to the retention times (RT), retention indices (RI) or typical ions in the chromatogram or mass spectrum, which the methods are to search for actively. However, the various methods for searching for target peaks or target substances lead to different statements, and to different quality of the statements.

Thus, according to the invention, two different evaluation devices are used, specifically a first evaluation device for deconvolution of the mass spectra obtained by the measurement device, and a second evaluation device for determining the intensity of the peaks, obtained by the measurement device, of the ions in the mass spectra. The (peak) assignments produced by these two evaluation devices are checked, and the respective assignments produced by the two evaluation devices are compared in a validation device provided for this purpose. This principle according to the invention improves the accuracy of the overall evaluation and assignment, by the use of different characteristics of the evaluation devices. In addition, false assignments are avoided, or at least reduced. The method can also be carried out automatically. Furthermore, the identification performance and the identification of substances contained in the sample are greatly improved.

This is particularly important when analyzing samples of biological materials, for example from plants, animals, microorganisms etc., in which many hundreds to a thousand compounds may be present. By way of example, this is necessary when searching for metabolites or new substances. The method is particularly suitable for automation, thus allowing high-efficiency analysis of a multiplicity of samples every day (High-Through-Put analysis, HTP). It will be virtually impossible—or even impossible—to cope with this amount of data manually. In addition to the plant extract areas mentioned exclusively in the description in the following text, and the search for substances in plants and marine sponges, the invention may, of course, also be used in all possible and feasible biological materials, in particular including tissue, bodily fluids, cell cultures, etc.

However, it is also possible and may be necessary within the scope of the invention to extend the described commercial evaluation devices AMDIS and/or (in particular) Chemstation by means of proprietary upgrades. These improvements relate in particular to determining match qualities (M2, see below). The evaluation devices (in particular Chemstation) can also be upgraded by determining a signal-to-noise ratio (S/N) and/or a blind value for the peaks.

In order to determine the signal-to-noise ratio, the noise for the ion signal of the peak is determined before and after the respective peak, using methods known to those skilled in the art such as peak-to-peak noise or root-mean-square noise (RMS), and by then calculating the respective signal-to-noise ratio before and after the peak, together with the peak signal intensity. This value which is obtained for a peak must exceed a predetermined limit if the peak is assigned to a substance and is intended to be reliably quantitatively evaluated. However, it is sufficient for the S/N ratio to exceed the limit value before or after the respective peak.

The signal intensity of a peak (peak height or peak area, or else the peak height or peak area normalized with respect to an internal standard) must furthermore also exceed a limit value for reliable quantitative evaluation, with this limit value being determined on a substance-specific and analysis-method-specific basis from the mean measured value of blank samples (blank value) and its standard deviation over a relatively long previous period.

These determinations are of interest because the S/N ratio and the signal intensity limit value to be exceeded are a gauge or bench mark of the quality of the measurement. For example, for the limit of detection, the reporting limit and the limit of quantitation of a peak, in particular of a peak (b) assigned to a substance by the second evaluation device (B), the values should be above a defined signal-to-noise ratio and a signal intensity limit value. This is the only way that it is possible to ensure that a signal or a peak has been correctly assigned to a substance and that the peak can be reliably quantitatively evaluated during subsequent analysis of the data.

A limit value for the S/N ratio and a limit value resulting from the blind value measurements (the latter on a substance-specific and analysis-method-specific basis) are therefore defined in each case for the limit of detection, the reporting limit and the limit of quantitation and must exceed the peak to be investigated. Otherwise, it is invalidated.

The defined signal-to-noise ratios and the signal intensity limit values of the peak therefore preferably increase in the following sequence: limit of detection, reporting limit, limit of quantitation. The limit of detection and reporting limit are therefore also passed through in a positive sense automatically, for example in a positive test of the limit of quantitation.

By way of example, commercially available SC/MS, LC/MS or HPLC/NS appliances are suitable for use as apparatuses for carrying out the method according to the invention. These normally have a processor (computer or data processing installation) which is able to carry out the method according to the invention when implemented in the form of a program (software). However, an embodiment in the form of programmable hard-wired logic modules would also be possible.

The invention also covers a computer program with program code which is suitable for carrying out a method according to the invention when the computer program is run on a suitable computation device. Both the computer program itself and the computer program stored on a computer-legible medium are claimed.

Programmable data processing installations are suitable for carrying out the method according to the invention and for use as the first and/or second evaluation devices.

Furthermore, the method according to the invention can be used to produce a graphics display of all the results (for example peak attributes, such as areas, relative and normalized and corrected areas, retention time, retention index etc.) in a manner that allows them to be restricted selectively on the basis of sample criteria (quality, sample type, test equipment, time period, etc.) and peak criteria (validity, evaluation type, etc.), thus simplifying and improving the optimization and analysis of the results.

A combination with quality analysis is also possible and worthwhile since this allows a high degree of automation to be achieved, thus allowing a high sample throughput with high result quality. Furthermore, this ensures that unknown substances, that is to say possible impurities or newly occurring signals of interest, which cannot be searched for deliberately without knowledge, are indicated by means of the method according to the invention and are therefore not "suppressed". Substances such as these which are indicated as newly occurring may be collected deliberately and automatically and are then used, together with their information such as mass spectrum, retention time, retention index and intensity, as a reference if the same substances occur once again later.

Furthermore, the validation device, to the extent that it appears to be useful, can also be used to calculate normalized or corrected values, for example for normalization of the peaks with respect to the intensity of a standard and/or with respect to the sample size (initial weight) and/or subtraction of blank value percentages of specific peaks with a measurement series.

The invention is also suitable for quality checking (assurance) by means of flexible rules (that is to say rules which can be combined freely), and an automatic limit-value check can also easily be incorporated, to be precise on a selectively different basis (that is to say different limit values) for specific analytes (that is to say samples and substances). Limit values may be checked, for example, on the basis of intensities, retention times, retention indices for individual peaks and, if appropriate, can be invalidated, or values for more than one sample, for example the recovery rate or the relative standard deviation of determined substance concentrations (for example from the peak intensities of the peaks for one analyte in all of the measurement samples or in the quality control samples in the sequence), can be calculated and checked against fixed limit values. If appropriate, this can be used to invalidate entire samples, fractions or groups of samples or fractions which do not satisfy the quality criteria defined in advance.

The method according to the invention is accordingly also suitable for analysis purposes when looking for substances in plants, marine sponges etc.

The method according to the invention defines peak-oriented and sample-oriented rules for checking the data (peaks) originating from the first and the second evaluation device. The use of individual rules is dependent on the respective substance (or peak) so that different rule combinations are worthwhile for different problems with different substances. There is no need to activate all of the rules, that is to say to use them for each sample or substance. In addition, the validation device does not need to apply all of the rules for each of the peaks assigned by the two evaluation devices. Specific rules are in each case applied only for the peaks assigned by one of the two evaluation devices, while others are applied for the peaks assigned by the respective other evaluation device, with yet others being applied for the peaks assigned by both evaluation devices.

This should be understood as meaning that only the respectively stated rules should be used, if only peaks of the first evaluation device or only peaks of the second evaluation device are dealt with in an isolated form in the validation device, that is to say no comparison is carried out between the respective peaks, either. The rules other than those stated would then in each case have no effect, even if they were activated.

It should also be mentioned that the rules can be modified, added to or extended in a simple manner at any time by virtue of the modular structure.

The invention will be described and explained in more detail in the following text using one exemplary embodiment and with reference to the attached drawings. The described and illustrated exemplary embodiment and the illustrated and explained sequence of rules according to the invention, and their content, should be regarded as an exemplary explanation of the invention, without any restriction to the subject matter of the invention as described in the patent claims.

FIG. 16 shows how a sample P is processed and analyzed, and how the resultant mass spectrum is evaluated, according to the present invention.

A sample P is passed in a manner known per se to a measurement device M which outputs mass spectra data D comprising a plurality of peaks. According to the invention, this mass spectra data D is supplied to two evaluation devices, specifically a first evaluation device A and a second evaluation device B.

The first evaluation device A deconvolutes the input mass spectra data D using a method as is known, by way of example, from the AMDIS system which has already been mentioned and described in the introduction. The second evaluation device B determines the intensity of the peaks contained in the mass spectra data D, using a method such as the Chem-station system which has already been mentioned and described in the introduction.

The assignment of the respective peaks a and b to substances which may be contained in the analyzed sample is produced as the output from the evaluation devices A and B. The peaks identified in this way are input to a validation device V for further evaluation and checking according to the invention.

Figure 1:
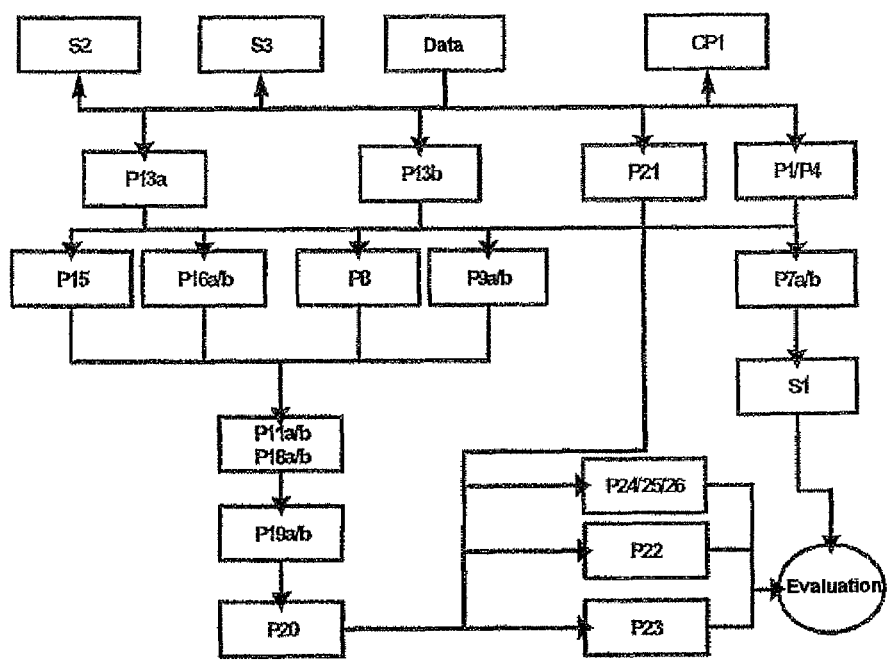
FIG. 1 shows a flowchart of a method according to the invention, and of rules contained therein.

FIG. 1 shows a sequence of various rules, which can be used as the basis for the check in the validation device V. The rules illustrated in FIG. 1 are listed in Table 1, for clarity reasons. In this case, a distinction can be drawn between so-called sample rules, whose numbering starts with the letter S, and so-called peak rules, whose numbering starts with the letter P.

The sequence of rules illustrated in FIG. 1 is not essential. The rules according to the invention may also be used in a different sequence. In particular, there is no need to activate all of the preceding rules in order to carry out a subsequent rule in the flowchart. The rules are therefore not dependent on one another.

There is no need for all of the rules to be activated, that is to say to be used for each sample or substance. In addition, the rules need not all be carried out for each of the peaks assigned by the two evaluation devices A and B. Certain rules are applied only for respective peaks assigned by one of the two evaluation devices, while others are applied for peaks assigned by the respective other evaluation device, with yet others being applied for peaks assigned by both evaluation devices.

Effective (that is to say eligible) rules for checking the peaks a from the first evaluation device A by means of the validation device are, in the present example, the Rules P4, P7b, P13a, P15, P16a, P16b, P18a, P18b, P19b and P22. Effective (that is to say eligible) rules for checking the peaks b from the second evaluation device B by means of the validation device in the present example are, analogously, the Rules P1, P21, P8, P9a, P9b, P11a, P11b and P23. The further peak rules are applied only when using both evaluation devices A, B(P19a, P7a), or are used independently of one another by both evaluation methods for the two evaluation devices A and B(P13b, P20).

The Rules P13a (only for the first evaluation device A), P13b (for both evaluation devices A, B) and P21 (only for the second evaluation device B) should sensibly be placed at the start of the process, but need not necessarily be applied to or activated for the following rules.

First of all, the Rule P1 should be checked for the second evaluation device B. The Rules P8, P9a/b, P11a/b can then be applied/combined (also jointly) as required. Considering just the sequence for the test procedure, the Rule P11a/b should be placed at the end, since this rule compares analytes with one another, and not just a single analyte with a defined standard. For this reason, it is worthwhile applying the Rules (P8,9a/b) for checking the RI (if they are activated) in advance, in order that the reference peak for Rule P11a/b (if it is activated) will have been checked as extensively as possible in advance.

An analogous situation applies to the first evaluation device A and the Rule P4. The Rules P15, P16a/b and P18a/b (P18a/b at the end, if activated) can then each be applied optionally or else in combination.

The comparisons by means of the Rules P7a with respect to the retention time (worthwhile mainly for time standards) and P19a with respect to the retention index between the evaluation devices A and B are, of course, worthwhile only when both methods of the evaluation devices A and B are also used.

However, the b Rule (7b and 19b) may in each case also be applied in an isolated form by the first evaluation device (A) so that peaks are invalidated independently by the second evaluation device (B) until only the one with the greatest intensity remains. It is worthwhile for the method comparisons P7a and P19a to be carried out after the actual individual checks P1/4 and P8/9/11/15/16/18, respectively, in the procedure. However, since these individual checks need not be activated, they are not an essential precondition for the comparisons.

A similar situation applies to the remaining Rules P22 (only for the first evaluation device A) and P23 (only for the second evaluation device B) as well as P20 and S1. It is worthwhile positioning them at the end of the sequence since they pass on the invalidation of peaks resulting from previous rules to further peaks or samples. In this case as well, activation of the previous rules is not an essential precondition.

First of all, the validation device uses Rule P1 or P4 to check whether the retention times of the respective peaks a and b assigned to substances by the respective first and second evaluation devices A and B are within defined limits. These limit values and the subsequent limit values may, for example, be predetermined by the user and may be stored in appropriate databases and, in the same way as all the parameters for peak checking rules (P1 to P23), are specific for the respective substance.

These two Rules P1 and P4 ensure that substances for which the time after which they will elute from the column of the chromatograph (in particular time standards) is known are released for further processing only if their retention times do not differ too much from the known times.

In parallel with this, the validation device uses Rule P13a to check whether the match qualities M1 of the peaks a assigned to a substance by the first evaluation device A are above defined limit values. The match quality takes account of the similarity of the spectrum found for a substance with a defined reference spectrum from a library, as well as the similarity of the retention index, defined in the same way in the library, to the experimentally found retention index. It is in the range from 0 to 100%, and is produced by the first evaluation device A. A minimum match between a spectrum that has been found and a reference spectrum can be ensured on the basis of this rule.

The following section relates to peaks a from the first evaluation device A and/or peaks b from the second evaluation device B, with the nature of the assignment of peaks to a substance differing, depending on the evaluation device A, B. These peaks which are assigned by the different evaluation devices using different methods are checked by means of Rule 13b for their match quality (M2) with a reference mass spectrum stored for that respective substance.

Thus, the validation device—likewise in parallel—uses Rule P13b to check whether the peaks a assigned to a substance on the basis of the match probability or match quality (M1) by the first evaluation device A and/or the second evaluation device B, as well as the peaks b assigned on the basis of the integration parameters, have a match quality (M2) above defined limit values. In this case, the match probability or match quality (M2) of the spectrum for a peak is checked statistically with the stored reference spectrum for the substance assigned to that peak by the first or the second evaluation device A or B, to be precise using a different, independent comparison method than that for Rule P13a (M1). The assignment is released for further processing only if the required accuracy (limit value) is exceeded or reached.

After one of the above steps, the validation device checks the peaks a, b assigned to the same substance, in particular a time standard, by the two evaluation devices A, B, by application of Rule P7a to determine whether their discrepancies from one another in the retention time (RT) are within defined limit values. This rule ensures that the respective peaks a and b assigned to one and the same sub-stance by the first and the second evaluation device A and B have retention times which do not differ excessively from one another, that is to say that, irrespective of the method, the peaks are located at a specific retention time or within specific limits around this retention time. This procedure is based on the finding that there can be only one correct retention time, since the retention times are independent of the subsequent evaluation method used for computation. Only minimal differences (resulting from the different calculation of the peak maximum) are permissible. For one substance, the retention times depend, so to speak, "only" on the chromatographic conditions.

However, as already mentioned above, the Rule P7a is not dependent on the previous rules, and can also be applied without activating these or carrying these out. A corresponding situation likewise applies to the following rules.

In the situation where the first evaluation device A has assigned a plurality of peaks a to the same substance, in particular a time standard, within defined limit values of the retention time, which peaks a have not yet been invalidated by the activated rules already applied before this rule (for example, comply with P7a, that is to say they are very closely adjacent and may represent possible false deconvolutions), the validation device furthermore uses Rule P7b to ensure that only that peak a with the largest area is processed further. This ensures that only the correct peak (or at least always the same peak with a high probability) can remain, in particular as one of the time standards for which further normalization and processing are used, and in any case only one peak can remain for one substance from the method used by the first evaluation device A, which peak is used, for example, as one of the time standards. Checking on the basis of their mass spectrum and their retention time is particularly important for time standards, since there is no calculated retention index for them, but only an associated retention index, whose checking would be pointless, although time standards are an important basis for checking the assignment for the other peaks, and must therefore be identified and checked reliably.

Furthermore, in order to ensure correct normalization and further processing by the validation device, Rule S1 is used to check whether the peaks found for a sample of time standards have been found by the second evaluation device B and have not yet been invalidated by the activated rules already applied before this rule. In other words, this ensures that every time standard that is required according to the method and has been specified in advance has also been recorded, and is valid in accordance with the rules which have already been applied.

In parallel with the checks (P13a, P13b, P1/4 and P7a/b and S1) described above, the validation device uses Rule P21 to ensure that the peaks b assigned to a substance by the second evaluation device B have no negative areas. Peaks with negative areas are either measurement errors or integration errors, and, since these must not occur, they must be excluded from further processing.

After checking the match quality (M1) by applying Rule P13a and/or (M2) by applying Rule P13b, it is possible for the validation device to next use Rule P15 to check whether the retention index (RI) of a peak a assigned to a substance by the first evaluation device A is within defined limit values. This ensures that only data is processed further for which there is certainty that the discrepancy between the target substance, which is being searched for by the first evaluation device A, and the substance found is not excessive. This procedure avoids false assignment.

After using Rule P13a to check the match quality (M1), and/or using Rule P13b to check (M2) and, for example, in parallel with the check of the retention index, the validation device uses Rule P16a/b (LIN_MOD) to check whether the retention index of the standard for linear modeling (LM-RI) and the retention index (RI) of a peak a which is assigned to a substance by the first evaluation device A lie, within defined discrepancies, adjacent to or on a straight line when plotted against one another (note: the retention index of the standard for linear modeling is referred to for simplicity in the following text as the linear model retention index).

According to the invention, it has been found that the retention indices of the peaks for one substance in the statistical evaluation may obey the linear regression rule, that is to say their values can be modeled as a linear function on the basis of a standard. A linear equation is therefore defined as the basis for these rules for a sub-stance to be tested for and for a standard defined experimentally in advance for this purpose, for plotting the RI of that substance against the RI of the standard for linear modeling (regression line with slope and intercept), with maximum permissible discrepancies being defined, and being stored in the database. Only if the values during checking (when the rules are applied) do not differ excessively from the linear equation, that is to say they are within the maximum predetermined discrepancies (limit values), do they actually belong to the substance being searched for, and can be released for further processing and analysis.

In this case, the standard may be a particular standard for linear modeling, or any given (suitable) substance contained in the sample. Linear modeling can be carried out as a peak test both for every standard assigned to the sample and for the other previously successfully checked (that is to say validated) peaks of target substances if a linear-modeling standard has been defined for them. As a standard for linear modeling, it is worthwhile defining in advance a peak which is found with a very high confidence level since, otherwise, the test for the substance to be tested will also have a negative result if the standard is not found. Furthermore, the chromatographic characteristics of the peak selected as the standard for linear modeling should be suitable for checking the respective peak, that is to say the more similar the chromatographical responses of the target substance being searched for and of the selected standard are (in general this means the more chemically similar they are), the more accurate is the linear modeling. In theory, it is possible to use a separate standard for each substance being searched for. A peak which is used as a linear-modeling standard in this case should not itself be checked by use of these rules, otherwise it will be necessary to adhere to a predefined sequence for application of these rules to test for the substances.

If a linear-modeling standard is predetermined as a parameter for a target substance, this is used to check the peaks a, b, otherwise the Rules P16a and P16b are skipped. If the linear-modeling standard itself is not found in the chromatogram, or the check has given a negative result on the basis of one of the previous rules, the linear modeling is concluded with a negative test result (this means that P16a is then noted as having failed, and P16b can no longer be checked at all). If the linear-modeling standard is found in the chromatogram and a check based on all the previous rules has been positive, then this linear-modeling standard is used to actually test the peak, with the linear modeling. The result of this test is then stored as a result relating to Rule P16b. The differentiation between the two Rules P16a and P16b is thus used in this case for documentation of which step in the test has failed. This also applies in an analogous manner to Rules P9a/b, P11a/b and P18a/b. In the case of Rules P7a/b, P13a/b and P19a/b, a and b each represent step elements for the respective rules, but the distinction between the step elements is located somewhere else, depending on the other contents of these rules.

Otherwise, the retention index $Y_{RI}$ of the target peak and the retention index $X_{RI}$ of the standard for linear modeling are compared with one another in the form of a linear equation, that is to say they are plotted against one another, in which case $$Y_{RI} < \alpha * X_{RI} + \beta + \text{Delta\_top}$$

and $$Y_{RI} > \alpha * X_{RI} + \beta + \text{Delta\_bottom}$$

must be satisfied. The parameters $\alpha$, $\beta$ and the maximum discrepancy delta in the upward and downward directions (which can be predetermined to have different magnitudes, Delta_bottom is negative) are predetermined for this purpose as target-peak-specific parameters. If the discrepancy of $Y_{RI}$ exceeds the respective delta, then the peak being examined is blocked for further analysis.

After checking the match quality of the match probability or quality (M2) using Rule P13b, the validation device uses Rule P8 to ensure that the retention index (RI) of a peak b assigned to a substance by the second evaluation device B is within defined limit values. This ensures that only data is further processed for which it is certain that the discrepancy between the target substance which the second evaluation device (B) is searching for and the substance found is not excessive. This procedure avoids false assignment. For peaks b from the second evaluation device B, the RI is calculated by the validation device V using the stated method, since type B evaluation devices generally have no RI values available.

Analogously to Rule P16a/b and in parallel with it, the validation device uses Rule P9a/b (LIN_MOD) to check whether the linear model retention index (LM-RI) and the retention index (RI) of a peak b which has been assigned to a substance by the second evaluation device B lie, within defined discrepancies, adjacent to or on a straight line when plotted against one another. For the details of this, reference should be made to the above statements relating to Rule P16a/b.

The validation device then checks the respective peaks a and b assigned to substances by the two evaluation devices A, B on the basis of Rule P11a/b and Rule P18a/b, respectively, to determine whether they have a defined neighbouring peak alongside them within defined limit values of the retention time, which has not yet been invalidated by the activated rules already applied before this rule. The chromatographic peaks of some substances have special features in that specific peaks always have a very specific neighbouring peak in specific investigated sample materials (matrices) before or after them. If a neighbouring peak such as this has been defined since it is known for the substance being searched for that it occurs close to the corresponding peak, and this does not appear within certain limits, then this supposedly does not relate to the sub-stance being searched for, and corresponding assignment of the peak would be false. These rules therefore allow high accuracy for substances whose peaks in the chromatogram have peak-neighbouring peak relationships such as these.

The validation device then uses Rule P19a to check the respective peaks a and b assigned to the same substance by the two evaluation devices A, B, to determine whether their discrepancies from one another in the retention index (RI) lie within defined limit values. This is because the peaks of a substance are located at a specific retention time or within certain limits around this retention time, irrespective of the method (there can be only one correct absolute retention time, since the retention times are independent of the subsequent evaluation method). Only minimal differences, resulting from the different calculation of the peak maximum, are permissible. The retention times for a sub-stance depend "only" on the chromatographic conditions.

Rule P19a is analogous to Rule P7a, with the difference that the retention index is used in this case instead of the retention time, indicating the position of the peak in a gas chromatogram, and to this extent having a similar function to an RT value (precisely speaking, analogous to the retention time). The retention index is characteristic of each substance and is highly dependent not only on the stationary phase used but also on the measurement temperature and the temperature program. It is determined by interpolation between the retention indices of the two compounds which are adjacent to the substance in the chromatogram and are added for this purpose, in general alkanes.

These compounds are generally added to the sample before the measurement (time standards), for example in the form of a homologous series of alkanes (possibly those alkanes with an odd number of carbon atoms in the chain). The retention indices for these reference compounds are fixed by definition (for 100*number of C atoms in the alkane); for example: RI (ethane)=200, RI (heptadecane)=1,700. The advantage of using the retention index is that it is normally more accurate than the retention time. It is also possible to use other homologous series instead of a homologous series of alkanes with an odd number of carbon atoms, for example saturated fatty acids with an odd number of carbon atoms or their methyl esters or amides, provided that they do not themselves occur as target substances of analytical interest in the sample.

At this point, it should be stressed that the present invention can be used not only as described in gas chromatography but also in liquid chromatography. In liquid chromatography, it may be worthwhile determining a fundamentally analogous retention index and using this to improve the data quality, in particular the correct assignment of sub-stances to peaks, by application of the appropriate peak rules. In this case, the retention index is influenced by a multiplicity of chromatographic parameters, for example including the eluent composition. In this case, any desired substances in the sample, preferably substances added to the sample, may be used as time standards, provided that they do not occur in the sample itself or do not represent target substances of interest in the sample. The time standards are then assigned to suitable fixed RI values, which are used to interpolate the RIs of the analytes.

The validation device then uses Rule P19b to ensure that, if the first evaluation device A has assigned the same substance to a plurality of peaks a which have not yet been invalidated by the activated rules already applied before this rule (for example complying with Rule P19a→are very closely adjacent and may represent false deconvolutions), only the peak (a) with the largest area is processed further. Despite the previous checking of the retention indices, it is possible for the first evaluation device A to find more than one peak within the above limit values, for example with this peak complying with Rule P19a. Rule P19b ensures that, in a situation such as this, only the peak with the largest area, that is to say that peak which has the highest probability of being the peak that is being searched for, may be used as the basis for further analysis. (This is based on the finding or assumption that, in fact, the smaller peaks represent false deconvolutions, and the largest has therefore a higher probability to be the correct peak. If the largest possible peak is always taken in all of the samples, then a peak which is comparable over all of the samples will always be reproducibly used for one specific substance.)

Furthermore, the validation device uses Rule P20 to check that a respective peak a or b which may have been assigned to a substance and has been found by the first or the second evaluation device A or B has not been normalized with respect to an internal standard peak (SP) which is not pre-sent or has not been successfully checked, that is to say that the quantitative result (intensity of a peak) for a substance has been normalized with respect to the quantitative result of an internal standard that is normally used for quantitative determination, but is false. It is possible for a standard (see above) which is present in the sample and its peak which the aim is to search for not to be found, or for a peak such as this not to have been released for further processing on the basis of the above rules, that is to say for it to have been invalidated. The other peaks must not be normalized with respect to a peak such as this, so that these peaks are likewise invalidated in the absence of the standard peak or if it is invalid.

Then, that is to say after Rules P20 and P21, the validation device uses Rule P22 to ensure that apart from any peak a assigned to a substance by the first evaluation device A, there is no validated unknown (that is to say not assigned to any substance) neighbouring peak within defined limit values (in particular within the RI or RT, preferably RI) whose mass spectrum also has a match quality (M2) above a defined limit value with the reference mass spectrum of the substance assigned to the peak a. For this rule, the defined limit values are very small, that is to say the check is carried out in the immediate vicinity of the peak a. The validation device uses these rules to investigate peaks which are not assigned to target substances, that is to say which are unknown. Unknown peaks such as these which occur in the immediate vicinity of a previously successfully checked peak for the same substance and also have a similar mass spectrum are eliminated, since the unknown peak already exists as a peak for the target substance. This avoids redundancy. In this case, it is desirable for unknown peaks which have a good match quality (=limit value, which is stored by the user) of the mass spectra with the adjacent identified peak not to be dealt with and therefore to be invalidated—"only" all others are potentially new and therefore very interesting substances which do not have a good match quality with known target substances.

In parallel with Rule P22, the validation device checks in Rule P23 that, apart from a peak b assigned to a substance by the second evaluation device B, there is no unknown peak (that is to say a peak not assigned to any substance but based only on non-specific integration of the total ion current (=TIC)) within defined limit values (in particular within the RI or RT, preferably RI), whose mass spectrum also has a match quality (M2) above a defined limit value with the reference mass spectrum of the substance assigned to the peak b. A person skilled in the art understands the expression TIC to be the total ion current, that is to say the sum of the intensities of all the ions plotted against time. For this rule, the defined limit values are likewise small, that is to say a check is carried out in the immediate vicinity of the peak (b). The second evaluation device B uses this rule to investigate peaks which are not assigned to target substances, that is to say which are unknown. Unknown peaks such as these which occur in the immediate vicinity of a peak which has already successfully been checked for the same substance and also have a similar mass spectrum are eliminated, since the unknown peak already exists as a peak of the target substance. This avoids redundancy when the match quality of the mass spectra of the unknown peak and peak b exceeds a stored limit value. This is therefore a rule analogous to Rule P22.

In parallel with Rules 22 and 23, the validation device uses Rules P24, P25 and P26, when using the second evaluation device B, to check whether a peak b which has been assigned to a substance by the second evaluation device B is in each case above a defined signal-to-noise ratio and a substance-dependent and analysis-method-dependent signal limit value for the limit of detection, the reporting limit and the limit of quantitation, respectively, for the peak b. These limits must be successfully reached by a peak since, otherwise, it is of only inadequate quality in order to be reliably assigned to one substance and to be reliably quantitatively evaluated during the final analysis of the data. This allows the measurement results for a sample to be checked for disturbing impurities, measurement errors and technical difficulties relating to the measurement.

The defined limits for the signal-to-noise ratios and the blind values in these rules rise in the following sequence: limit of detection, reporting limit, limit of quantitation. The rules relating to the limit of detection P24 and the reporting limit P25 are therefore applied successfully if the Rules P26 relating to the limit of quantitation have been successfully completed. If Rule P26 has been applied with a negative result, then the peak for a substance cannot reliably be quantitatively evaluated. If Rules P25 or even P24 have also been applied with a negative result, the peak can then be quantitatively evaluated only with low reliability (P25) or the assignment to a substance may even be unreliable (P24), and the other rules possibly need then not be evaluated.

The validation device releases the respectively successfully checked peaks of the deconvoluted mass spectra signals a and of integrated ions b for further analysis only if all of the activated rules have been checked successfully.

The proposed method therefore reduces, possibly automatically, the number of peaks to be analyzed in a chromatogram or mass spectrum, since invalid peaks, which have been blocked from or not released for further processing by the method according to the invention, are identified as such. This simplifies, speeds up and improves the analysis of complex mixtures.

The method and system according to the invention can also be included in a laboratory information management system (LIMS), so that it is possible to check the sample tracking data, such as fresh weight, measurement methods and sequence relationship. By way of example, this means that, in parallel with the rules that have been explained, it is possible to check whether a sample which has been fractionated before the analysis has peaks in fractions which have been marked as missing or as false measurements, for example those which have been found to be false and marked fractions during previous quality control of the measurement data. This must not be the case, of course, and peaks such as these must therefore be excluded from the further analysis (Rule S2).

On the other hand, fractions which have been identified as being present must have at least one peak in their spectra (Rule CP1). If no peaks relating to an existing fraction are accordingly found, then, if appropriate, a warning message can inform the user of possible problems.

Furthermore samples which have no fresh weight (for example errors in determining the fresh weight) can not produce valid peaks (Rule S3). If a situation such as this occurs, all of the peaks for that sample must be blocked from further processing.

This process of embedding the check of the spectroscopic data in a laboratory information system allows comprehensive checking and sample tracking despite a large number of samples, as is the situation nowadays for highthroughput analysis.

FIGS. 2 to 7 show the application of Rules P8 and P20 by the validation device to peaks b which the second evaluation device B has assigned to an internal standard or a substance X.

Figure 2:
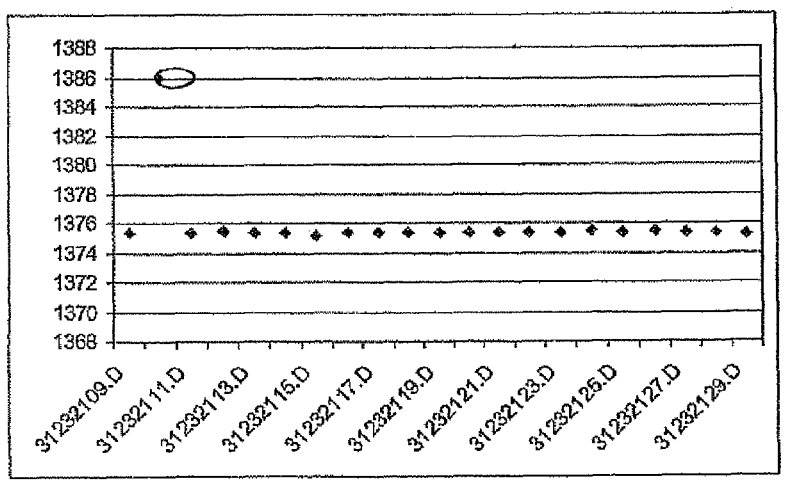
FIGS. 2 to 7 show the application of Rules P8 and P20 of FIG. 1 to the mass spectra data from a plurality of samples.

FIG. 2 shows the plot for the retention index of the peaks for a substance in different samples against the identification number of the samples, with the substance being an internal standard (ISTD), and with the second evaluation device B having assigned the peaks to that standard. As can be seen, the retention index for the peak from the internal standard in one sample (31232110.D) differs to a major extent from those for the others, that is to say it is not in the (predetermined) expected range. This peak is therefore not suitable for use as an internal standard in the corresponding sample, since an error has obviously occurred in the measurement. Errors such as these can be corrected by the validation device by using the activated Rule P8 to invalidate the corresponding peak. As mentioned above, Rule PB results in invalidation of peaks for a sub-stance which do not occur in the expected retention index range.

Figure 3:
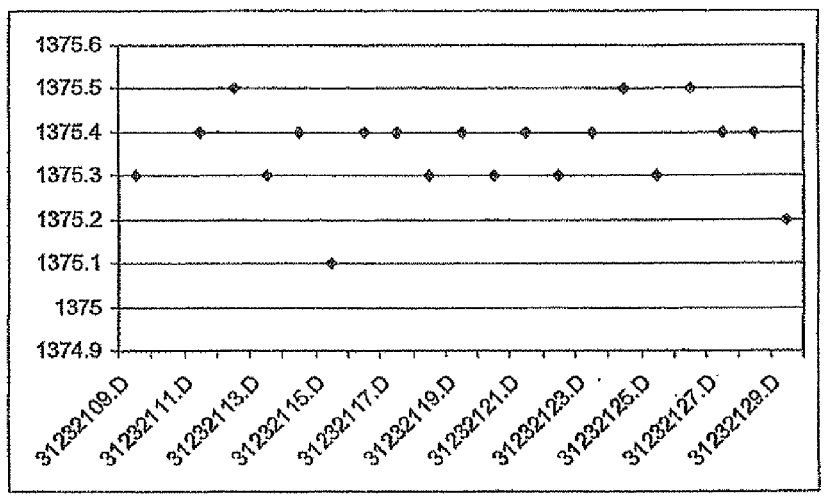

FIG. 3 shows the result of the validation device applying Rule P8 to the samples shown in FIG. 2. The peak with a major discrepancy in the internal standard in the sample in question has been invalidated, that is to say it is no longer considered in the further processing. In order to identify this, the data point or peak (circled in FIG. 2) has been removed from the graph (FIG. 3). In order to improve the representation, the scale of the graph has been changed from that in FIG. 2.

Figure 4:
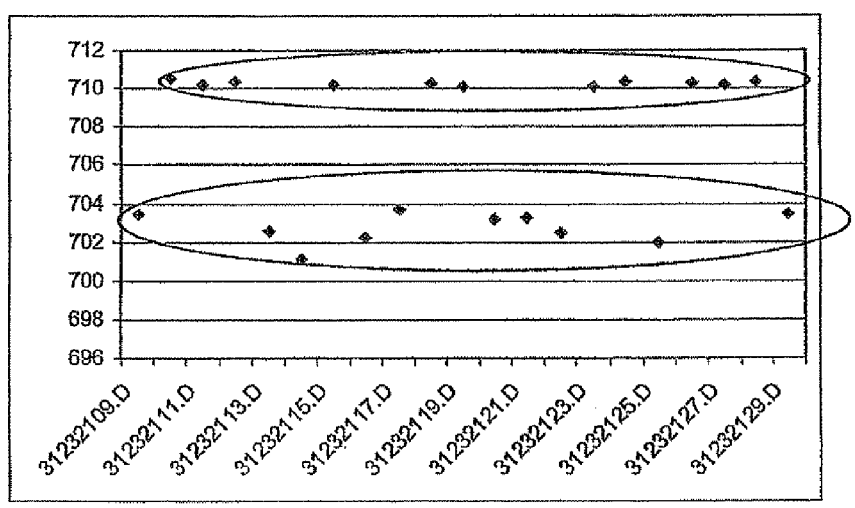

FIG. 4 shows a corresponding view of the retention indices which have been assigned to a substance X by the second evaluation device B in a plurality of samples, with these being the same samples as those in FIGS. 2 and 3, but with the difference that the investigation has been carried out for the substance X rather than the internal standard.

Figure 5:
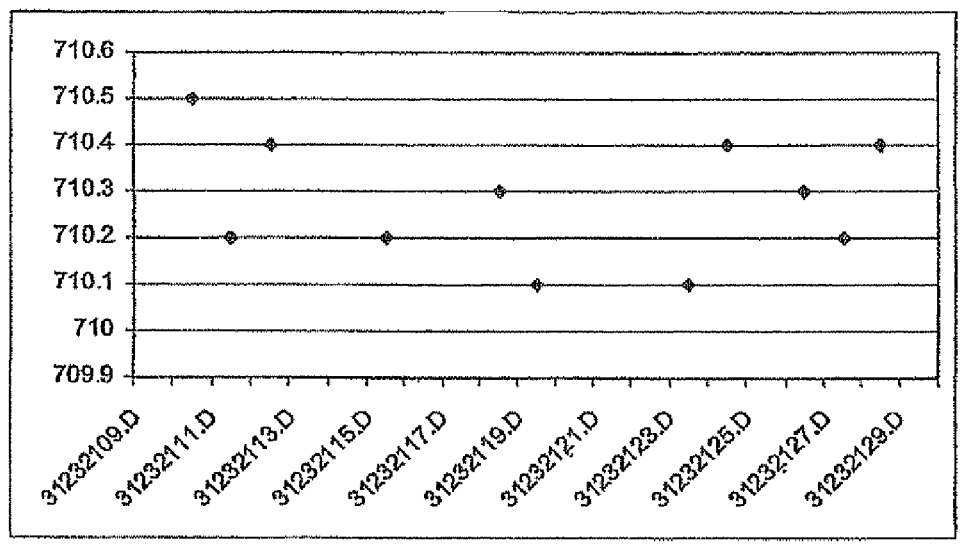

This clearly shows that there are two groups of retention indices. One group of indices is located around 710, while the second group is arranged, with a somewhat broader scatter, around the value 703. It is therefore probable that this does not relate to a single substance X, but to two different substances. By way of example, such an occurrence of two groups of retention indices for the peaks assigned to one substance in different samples can occur if peaks are falsely assigned to the substance by the second evaluation device B because the concentration of the substance in the sample is too low. In this situation, it is therefore also worthwhile for the validation device to apply Rule P8 in order to exclude one of the groups of retention indices from further processing. In the present case, those peaks whose retention index is outside the range from 709.9 to 710.9 are invalidated. FIG. 5 shows the graph (on an adapted scale) after application of Rule P8 and after removal of invalidated peaks. These peaks in the second group are now excluded from further processing (analysis and evaluation) for the substance X.

Figure 6:
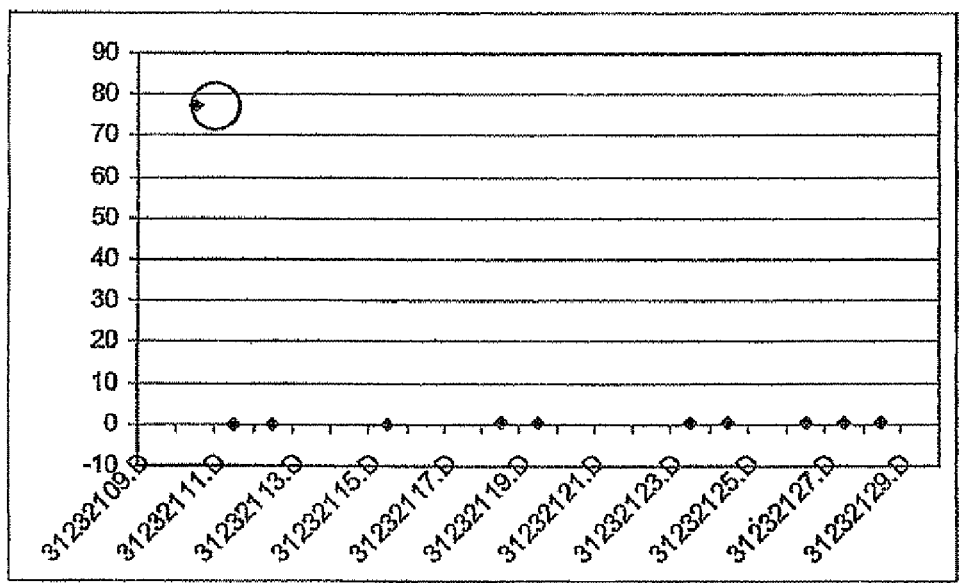
Figure 7:
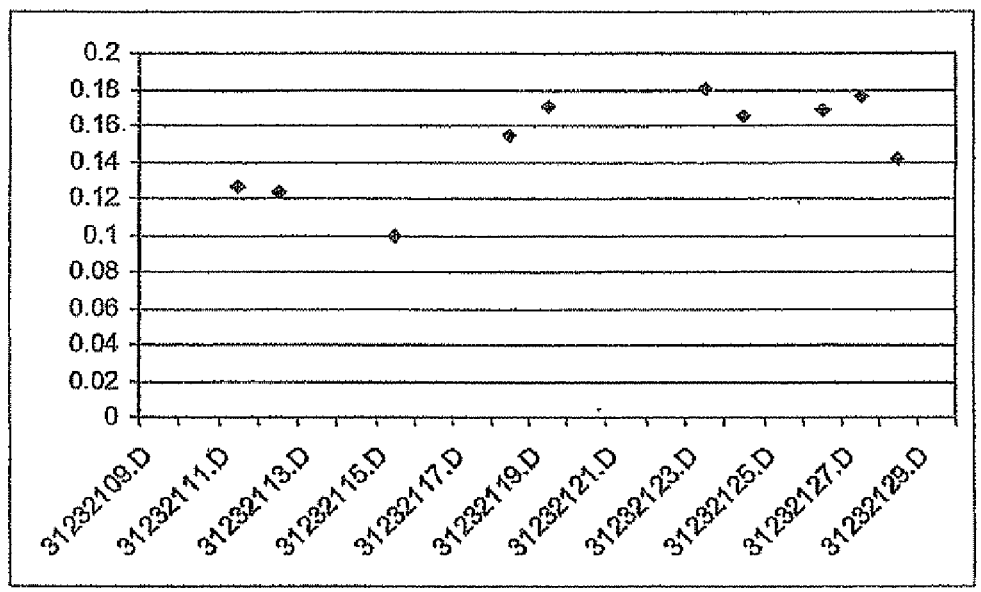

Instead of the retention indices, FIG. 6 shows the relative normalized area (intensity normalized with respect to the internal standard) for the peaks assigned to the sub-stance X, in the various samples. As can be seen, despite the application of Rule P8 by the validation device, there are still major discrepancies in terms of the relative area of the peak, in one sample. It is therefore probable that this value is erroneous. The sample is the same as the sample already marked in FIG. 2, for which the internal standard has been invalidated. In this case, the validation device can then exclude falsely assigned peaks from further processing by application of Rule P20. (According to Rule P20, when the first and/or the second evaluation device A or B, respectively, is used, a check is carried out to determine whether a respective peak a or b assigned to a sub-stance by the first or the second evaluation device A, B has not been normalized with respect to a standard peak (SP) which is not present or a standard peak (SP) which has not been successfully checked by previously applied and activated rules). As can be seen from FIG. 7, this means that the corresponding peak is invalidated in the sample in question. The peak for the sample in question has therefore been removed from the graph, and the scale for the graph has been adapted once again.

Figure 8:
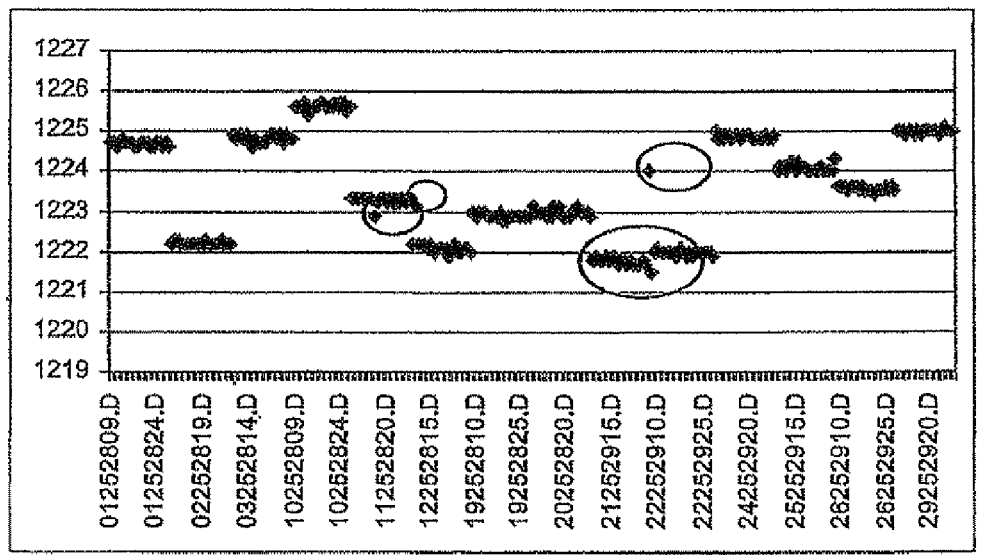
FIGS. 8 to 10 show the application of Rules P1 S1 and S2 of FIG. 1 to the mass spectra data from a plurality of samples.
Figure 9:
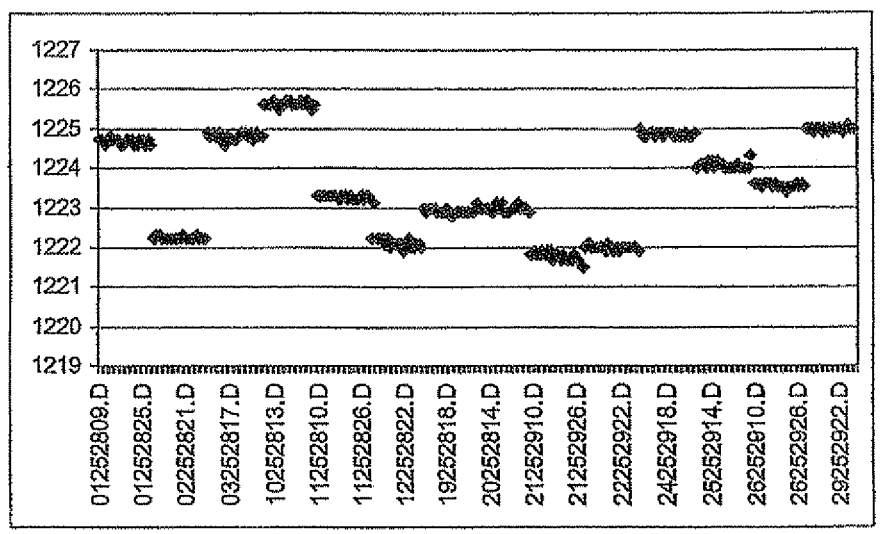
Figure 10:
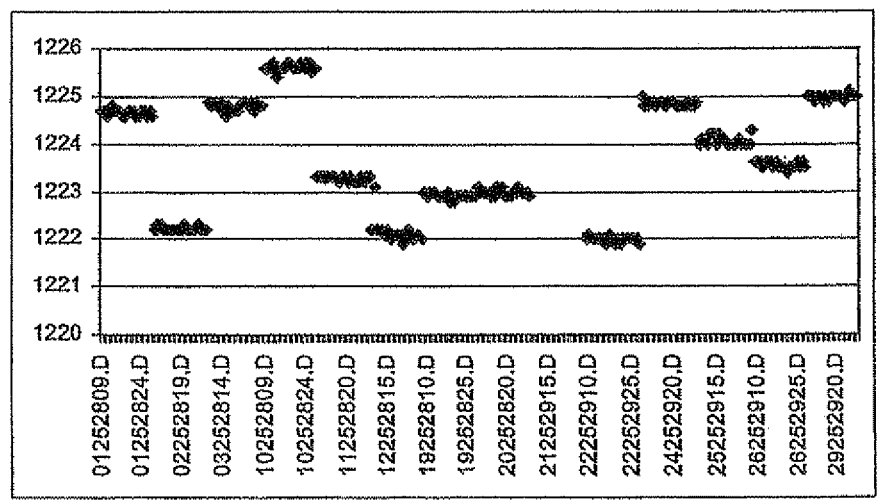

FIGS. 8 to 10 show the application of Rules S1, S2 and P1 and P20 by the validation device to peaks which have been assigned to a substance Y by the second evaluation device B.

FIG. 8 shows the retention indices for the peaks of different samples assigned to the substance Y by the second evaluation device B. There are a plurality of groups of retention indices for the peaks for the substance Y. This can occur, for example, because different equipment (GCMS) has been used for carrying out the chromatography and for recording the mass spectra. A further reason may result from the phases of the columns used. Although the same phases are used in order to keep discrepancies in the results small, it is nevertheless possible for discrepant results (RI) to be obtained on different columns for one and the same substance. This is a result, for example, of the different life and wear, contamination, phase material destruction (bleeding), temperature and/or pressure fluctuations etc. Those skilled in the art will be familiar with effects such as these, and their effects.

Once the validation device has applied Rule S2 in the LIMS, samples which have been marked as erroneous or false are invalidated, that is to say those samples for which an error has occurred during sample preparation or measurement and has been noted and recorded in the LIMS (i.e. those which may produce no peaks but have nevertheless been included in the measurement and have been passed to the validation device) are invalidated. As illustrated in FIG. 9, a plurality of samples (circled in FIG. 8) have been invalidated in response to this. In the case of the high throughput methods used nowadays in biological research, in which several thousand samples must be processed and analyzed every day, it is possible for errors such as these to actually occur and, if they are not detected, these errors will subsequently frequently lead to consequential errors, which are difficult to detect and rectify, during analysis. The possibility for automatic invalidation of such false samples at an early stage is therefore a major advantage for HTP analysis.

If the validation device V applies Rule S1 to the groups of peaks illustrated in FIG. 8, that is to say samples for which at least one time standard has not been found or which has not previously been successfully checked for by means of Rule P1, are invalidated, then this results in the plot shown in FIG. 10. In addition to one complete group of peaks or samples (circled in FIG. 8), further individual peaks (or samples) have also been invalidated which would at least partially have already been invalidated in parallel (independently) by Rule S2. Samples in which the (obligatory) time standards have not been found offer only poor capabilities for normalization and definition of the retention indices, etc., so that it is quite worthwhile to mark these as being erroneous or false, and thus to invalidate them. If required, it may be possible to measure them once again after checking.

Figure 11:
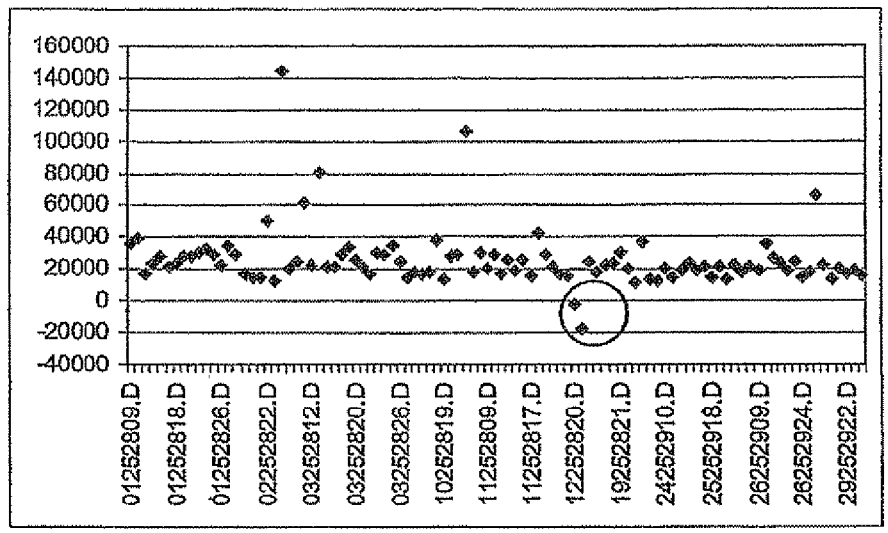
FIGS. 11 and 12 show the application of Rule P21 of FIG. 1 to the mass spectra data from a plurality of samples.
Figure 12:
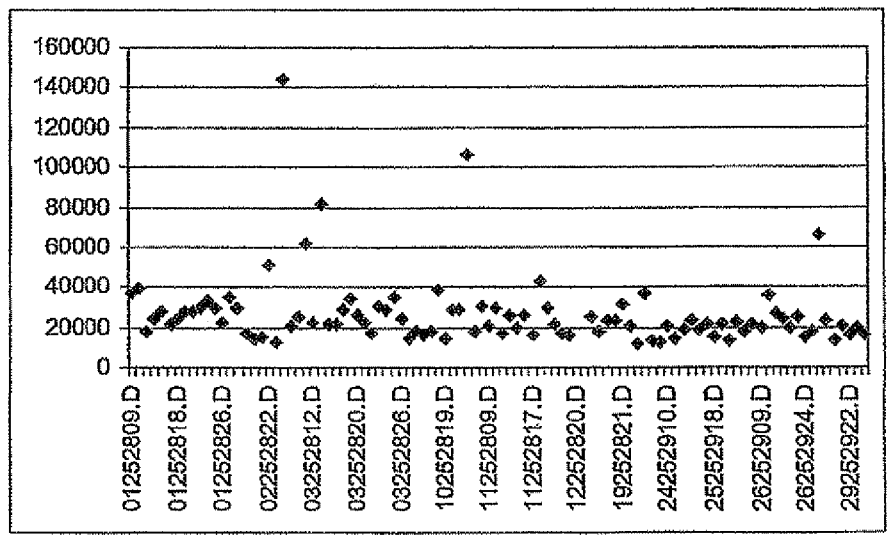

FIGS. 11 and 12 show the application of Rule P21 by the validation device to peaks which have been assigned to a substance Z by the second evaluation device B.

FIG. 11 shows a plot of the absolute area of the peaks assigned to the substance Z for different samples. In the illustrated example, the area of two peaks (circled) is close to zero, or may be negative. By definition, a negative area cannot occur, and signals and peaks such as these must therefore be excluded from further evaluation. The validation device can use Rule P21 to check this, and to invalidate peaks with negative areas. As can be seen in FIG. 12, both of the peaks in question from FIG. 11 had a negative area, and were therefore invalidated by the validation device despite the assignment produced by the second evaluation device B.

Figure 13:
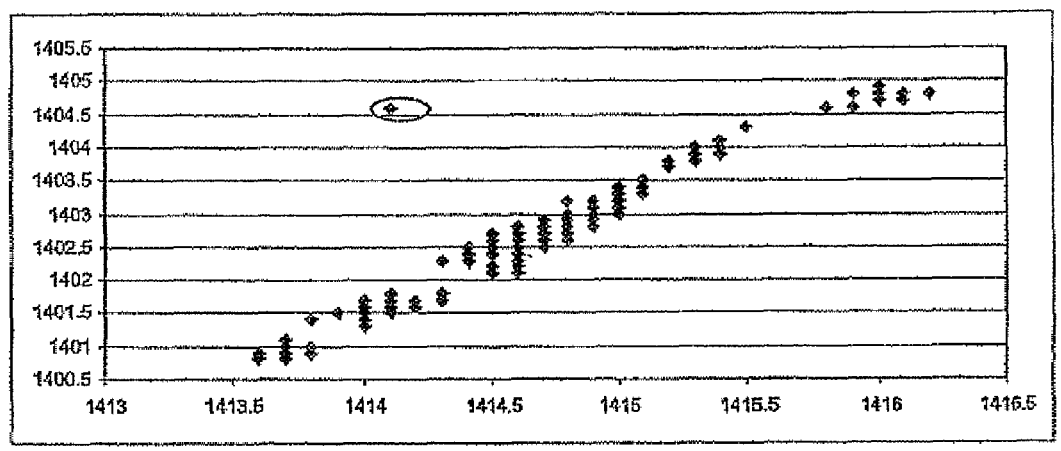
FIGS. 13 to 15 show the application of a linear modeling based on Rule P9a of FIG. 1 to the mass spectra data from a plurality of samples.
Figure 14:
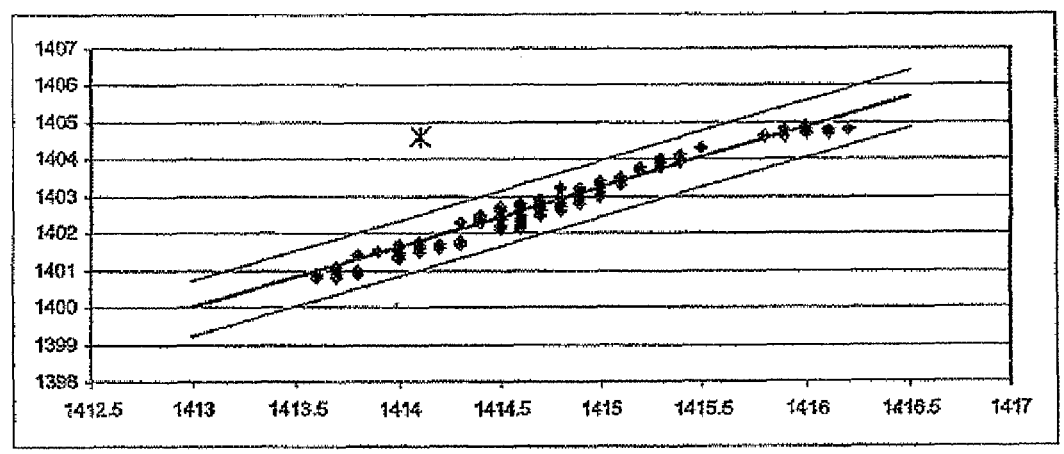

FIGS. 13 and 14 show the use of linear modeling to check a substance W. The plot shows the retention index of the peaks assigned to the substance W against the retention index of the peaks for the linear-modeling standard. As explained above, the validation device uses Rule P9a/b (or Rule P16a/b) to check whether the linear model retention index (LM-RI) and the retention index (RI) of a respective peak b or a assigned to a substance by one of the two evaluation devices B or A lie, within defined limits, on or adjacent to a straight line, that is to say lie within a corridor around a straight line.

Figure 15:
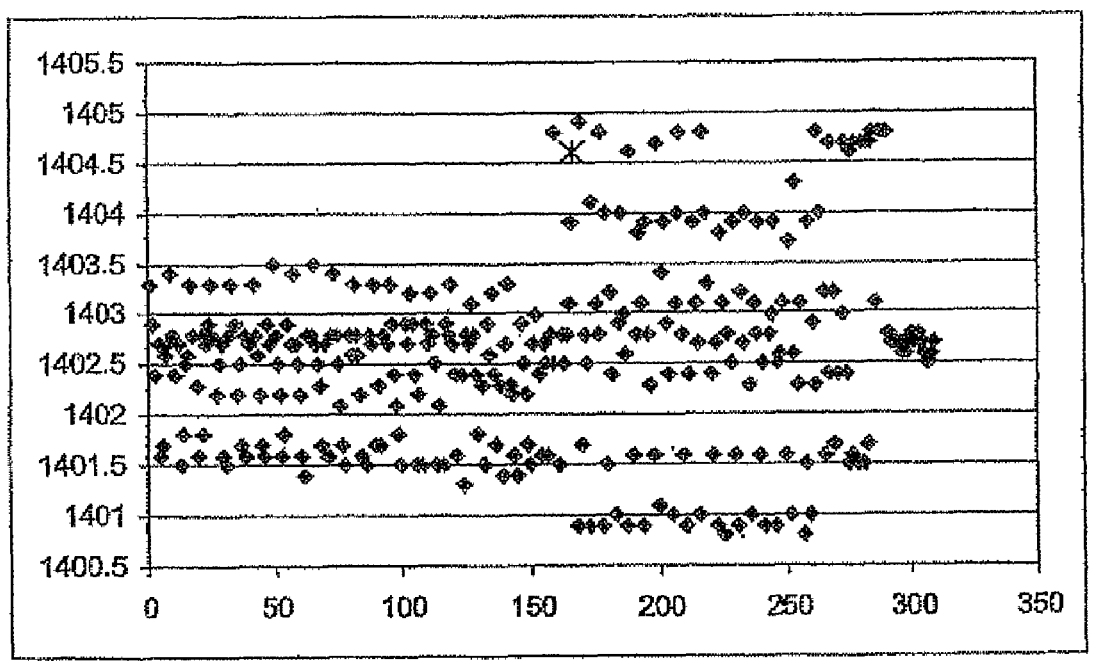
Figure 16:
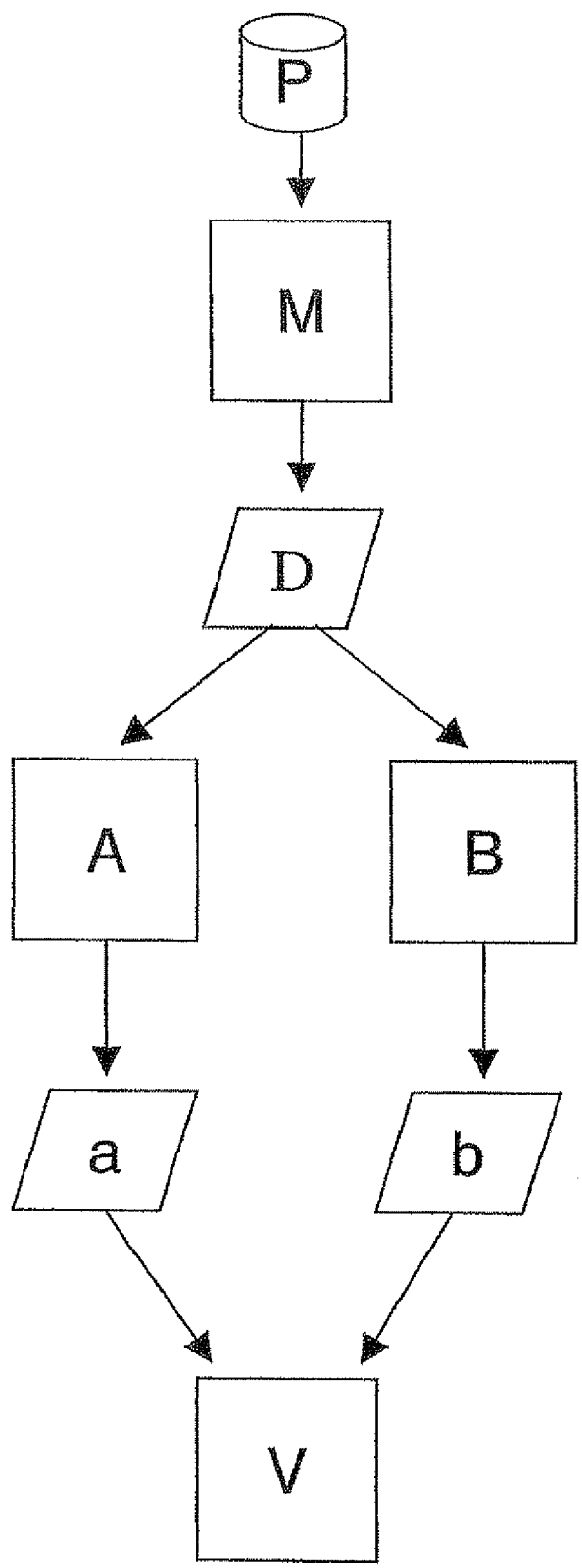
FIG. 16 shows a schematic procedure for the analysis and evaluation principle according to the invention.

The plot results approximately in a straight line, with, in the illustrated situation, only minor discrepancies from linear modeling throughout the entire retention index range for the substance in comparison to the scatter occurring, as can be seen from FIG. 14, in which the linear regression line and the limit values (Delta_top/bottom) are shown. In comparison to this, the scatter for the "normal" plot (see FIG. 15: RI against measurements) is so great that it is impossible to reliably assign the peaks to the substance W. The data point or peak (circled or a star) marked in FIGS. 13 to 15 could not be removed from the evaluation if conventional methods or conventional procedures were used (FIG. 15). The data point in question is, as can be seen, located in between the other valid points and therefore cannot be directly selected for invalidation.

Linear modeling is highly suitable in particular for determining the identity of the assigned peaks for peaks located closely adjacent to one another of substances such as those which occur, for example, in the case of isomers with an RI difference of less than 3, even though this would not be feasible on the basis of the absolute retention indices.

The invention claimed is:

1. A method for analyzing a sample containing a plurality of substances, comprising:
acquiring mass spectra (mass spectra data D) of the sample (P) received from an upstream chromatograph by means of a measurement device (M),
assigning chromatographic peaks (a) and (b) and their associated mass spectra to a respective one of the substances, wherein the assignment is performed in at least one of a first evaluation device (A) and a second evaluation device (B), with the first evaluation device (A) comprising at least one comparing device for comparing the deconvoluted mass spectra with stored reference spectra, and with the second evaluation device (B) comprising at least one comparing device for comparing the mass spectra of the chromatographic peaks of the ions with stored reference spectra;
wherein assigning chromatographic peaks includes, in the first evaluation device (A), deconvoluting the mass spectra obtained by the measurement device (M) and assigning the chromatographic peaks (a) and their associated deconvoluted mass spectra to a respective one of the substances on the basis of a match with a reference spectrum of that substance; and
wherein assigning chromatographic peaks includes, in the second evaluation device (B), determining the intensity of the peaks, obtained by the measurement device, of the ions in the mass spectra, with ions which are specific for the substance and with their retention time range being preset, and assigning the chromatographic peaks (b) of the ions and their associated mass spectra to the reference values, predetermined for a substance, of that substance on the basis of a match between selective ions and their retention time ranges of the peaks (b); and
checking the performed assignments of at least one of the first evaluation device (A) and the second evaluation device (B) in a validation device (V) at least on the basis of peak-oriented rules.

2. The method of claim 1, in which, when the first evaluation device (A) is used, a check is carried out in the validation device (V) to determine whether the retention times of the peaks (a) assigned to substances by the first evaluation device (A) are within defined limits (Rule P4).

3. The method of claim 1, in which, when the second evaluation device (B) is used, a check is carried out in the validation device (V) to determine whether the retention times of the peaks (b) assigned to substances by the second evaluation device (B) are within defined limits (Rule P1).

4. The method of claim 1, in which, when the first evaluation device (A) is us1d, a check is carried out in the validation device (V) to determine whether the match qualities (Ml) of the peaks (a) assigned to a substance by the first evaluation device (A) are above defined limit values (Rule P13a).

5. The method of claim 1, in which, when either of the first or the second evaluation device (A, B) is used, a check is carried out in the validation device (V) to determine whether the match qualities (M2) of the respective peaks (a or b) assigned to a substance by one or more of the evaluation device (A and B) are above defined limit values (Rule P13b).

6. The method of claim 1, in which the respective peaks (a or b) assigned to the same substance by the two evaluation devices (A and B) are checked in the validation device (V) to determine whether their discrepancies or deviations from one another in the retention time (RT) are within defined limit values (Rule P7a).

7. The method of claim 1, in which, in the situation where the first evaluation device (A) has assigned a plurality of peaks (a) to the same substance, which peaks have not yet been invalidated by the activated rules already applied before this rule, only that peak (a) with the largest area is processed further in the validation device (V) (Rule P7b).

8. The method of claim 1, in which, when the second evaluation device (B) is used, a check is carried out in the validation device (V) to determine whether the peaks found for a sample (P) have been found for time standards by the second evaluation device (B), and have not yet been invalidated by the activated rules already applied before this rule (Rule S1).

9. The method of claim 1, in which, when the first evaluation device (A) is used, a check is carried out in the validation device (V) to determine whether the retention index (RI) of a peak (a) assigned to a substance by the evaluation device (A) is within defined limit values (Rule P15).

10. The method of claim 1, in which, when the first evaluation device (A) is used, a check is carried out in the validation device (V) to determine whether the retention index of the standard for linear modeling (LM-RI) and the retention index (RI) of a peak (a) which is assigned to a substance by the first evaluation device (A) lie, within defined tolerances, adjacent to or on a straight line when plotted against one another (Rule P16a/b (LIN_MOD)).

11. The method of claim 10, in which the standard is a particular standard for at least one of linear modeling and any given substance.

12. The method of claim 1, in which, when the second evaluation device (B) is used, a check is carried out in the validation device (V) to determine whether the retention index (RI) of a peak (b) assigned to substances by the second evaluation device (B) is within defined limit values (Rule P8).

13. The method of claim 1, in which, when the second evaluation device (B) is used, a check is carried out in the validation device (7) to determine whether the retention index of the standard for linear modeling (LM-RI) and the retention index (RI) of a peak (b) which has been assigned to a substance by the second evaluation device (B) lie, within defined tolerances, adjacent to or on a straight line when plotted against one another (Rule P9a/b (LIN_MOD)).

14. The method of claim 13, in which the standard is a particular standard for at least one of linear modeling and any given substance.

15. The method of claim 1, in which the peaks (a) assigned to substances by the first evaluation device (A) are checked in the validation device (V) to determine whether they have a defined neighbouring peak alongside them between defined minimum and maximum values of the retention time on a defined side (Rule P18a/b) and which neighbouring peak has not yet been invalidated by the activated rules already applied before this rule.

16. The method of claim 1, in which the peaks (b) assigned to substances by the second evaluation device (B) are checked in the validation device (V) to determine whether they have a defined neighbouring peak alongside them between defined minimum and maximum values of the retention time on a defined side (Rule P11a/b) and which neighbouring peak has not yet been invalidated by the activated rules already applied before this rule.

17. The method of claim 1, in which, when the evaluation devices (A and B) are used, the respective peaks (a and b) assigned to the same substance by both evaluation devices (A and B) are checked in the validation device (V) to determine whether their discrepancies or deviations from one another in the retention index (RI) lie within defined limit values (Rule P19a).

18. The method of claim 1, in which, in the situation where the first evaluation device (A) has assigned the same substance to a plurality of peaks (a) which have not yet been invalidated by the activated rules already applied before this rule, only the peak (a) with the largest area is processed farther in the validation device (V) (Rule P19b).

19. The method of claim 1, in which, when either of the first or the second evaluation device (A, B) is used, a check is carried out in the validation device (V) to determine whether a respective peak (a or b) which has been found by at least one of the first evaluation device (A) and the second evaluation device (B) and may have been assigned to a substance has not been normalized with respect to a standard peak (SF) which is not present or a standard peak (SP) which has not been successfully checked by rules that have previously been applied and activated (Rule P20).

20. The method of claim 1, in which, when the second evaluation device (B) is used, a check is carried out in the validation device (V) to determine whether the peaks (b) assigned to a substance by the second evaluation device (B) have no negative areas (Rule P21).

21. The method of claim 1, in which, when the first evaluation device (A) is used, a check is carried out in the validation device (V) to determine whether a peak (a) which has not been assigned to any substance by the first evaluation device (A), that is to say an unknown peak (a), has no validated known neighbouring peak within defined limit values, whose reference spectrum also has a match quality above a defined limit value with the mass spectrum of the unknown peak (a) (Rule P22).

22. The method of claim 1, in which, when the second evaluation device (B) is used, a check is carried out in the validation device (V) to determine whether a TIC peak (b) which has not been assigned to any substance by the second evaluation device (B) has no validated known neighbouring peak within defined limit values, whose reference spectrum also has a match quality above a defined limit value with the mass spectrum of the unknown TIC peak (b) (Rule P23).

23. The method of claim 1, in which, when the second evaluation device (B) is used, a check is carried out in the validation device (V) to determine whether a peak (b) which has been assigned to a substance by the second evaluation device (B) is above a defined signal-to-noise ratio and a signal intensity value for the limit of detection of the substance (Rule P24).

24. The method of claim 23, in which the defined signal-to-noise ratios and the signal intensity values rise in the sequence limit of detection, reporting limit, limit of quantitation, and may differ corresponding to the substance assigned to a peak.

25. The method of claim 1, in which, when the second evaluation device (B) is used, a check is carried out in the validation device (7) to determine whether a peak (b) which has been assigned to a substance by the second evaluation device (B) is above a defined signal-to-noise ratio and a signal intensity value for the reporting limit of the substance (Rule P25).

26. The method of claim 1, in which, when the second evaluation device (B) is used, a check is carried out in the validation device (V) to determine whether a peak (b) which has been assigned to a substance by the second evaluation device (B) is above a defined signal-to-noise ratio and a signal intensity value for the limit of quantitation of the substance (Rule P26).

27. The method of claim 1, in which only the respective peaks checked successfully by activated rules in the evaluated and deconvoluted mass spectra signals are released for further evaluation.

28. A programmable data processing installation for carrying out a method of claim 1.

29. A computer program with program code which is suitable for carrying out a method of claim 1 when the computer program is run on a data processing installation which is suitable for this purpose, or in a laboratory system which is suitable for this purpose.

30. A computer-readable medium having a computer program of claim 29 stored on it.

31. The method of claim 1, in which, when the first evaluation device (A) is used to assign the retention index (RI) of a peak (a) to a substance, deconvolution settings for the evaluation device (A) are preset.

32. The method of claim 31, in which, when the first evaluation device (A) is used to assign the retention index (RI) of a peak (a) to a substance, one or more of a reference spectra, calibration for the retention index (RI), and values of the retention index (RI) for substance identification are preset.

33. A mass spectrometry analysis system for analyzing a sample containing a plurality of substances, according to a method of claim 1, comprising
- a measurement device (M) for acquiring mass spectra from the sample (P) obtained from an upstream chromatograph,
- at least one of a first evaluation device (A) and a second evaluation device (B), the first evaluation device (A) being for deconvoluting the mass spectra obtained by the measurement device (M), with at least one comparing device for comparing the deconvoluted mass spectra with stored reference spectra, and the second evaluation device (B) being for determining the intensity of the peaks, obtained by the measurement device (M), of the ions in the mass spectra, if appropriate with ions which are specific for that substance and their retention time range being preset, with the second evaluation device (B) having at least one comparing device for comparing the mass spectra of the chromato graphic peaks of the ions with stored reference spectra, wherein
  - an assignment of the chromatographic peaks (a) and their associated deconvoluted mass spectra to a respective one of the substances in the first evaluation device (A) is performed on the basis of the match with a reference spectrum for the substance, and
  - an assignment of the chromatographic peaks (b) of the ions and their associated mass spectra to a respective one of the substances in the second evaluation device (B) is performed on the basis of the match between selective ions and their retention time ranges of the peaks (b) with the reference values predetermined for a substance; and
  - a validation device (V) for checking the performed assignments of at least one of the first evaluation device (A) and the second evaluation device (B) at least on the basis of peak-oriented rules.

34. The mass spectrometry analysis system of claim 31, comprising at least one programmable data processing installation as the first and/or the second evaluation device (A and/or B), respectively.

35. A laboratory information management system (LIMS) comprising a mass spectrometry analysis system of claim 31.

36. The use of claim 31, in which the sample to be analyzed is a plant extract.

37. The mass spectrometry analysis system of claim 33, wherein when the assignment of the chromatographic peaks (a) and their associated deconvoluted mass spectra is performed to one of the substances in the first evaluation device (A), deconvolution settings for the the first evaluation device (A) are preset.

38. The mass spectrometry analysis system of claim 33, wherein when the assignment of the chromatographic peaks (a) and their associated deconvoluted mass spectra is performed to one of the substances in the first evaluation device (A), one or more of a reference spectra, calibration for the retention index (RI), and values of the retention index (RI) for substance identification are preset.

* * * * *